United States Patent [19]

Schlief

[11] Patent Number: 5,380,411
[45] Date of Patent: Jan. 10, 1995

[54] ULTRASOUND OR SHOCK WAVE WORK PROCESS AND PREPARATION FOR CARRYING OUT SAME

[75] Inventor: Reinhard Schlief, Berlin, Germany

[73] Assignee: Schering Aktiengesellschaft, Berlin and Bergkamen, Germany

[21] Appl. No.: 548,912

[22] PCT Filed: Dec. 2, 1988

[86] PCT No.: PCT/DE88/00750
§ 371 Date: Aug. 2, 1990
§ 102(e) Date: Aug. 2, 1990

[87] PCT Pub. No.: WO89/05159
PCT Pub. Date: Jun. 15, 1989

[30] Foreign Application Priority Data

Dec. 2, 1987 [DE] Germany ............... 3741201

[51] Int. Cl.$^6$ .............................................. C07C 1/00
[52] U.S. Cl. ................. 204/157.15; 604/22; 606/128; 601/2; 601/4
[58] Field of Search .............. 604/22; 606/128; 128/24 AA, 24 EL, 804; 204/157.15

[56] References Cited

U.S. PATENT DOCUMENTS

| | | | |
|---|---|---|---|
| 4,276,885 | 7/1981 | Tickner et al. | 128/660 |
| 4,466,442 | 8/1984 | Hilmann | 128/653 |
| 4,681,119 | 7/1987 | Rasor | 128/660 |
| 4,920,954 | 5/1990 | Alliger et al. | 128/24 AA |

FOREIGN PATENT DOCUMENTS 1232837 2/1988 Canada .
1239092 7/1988 Canada .

*Primary Examiner*—Kathryn Gorgos
*Attorney, Agent, or Firm*—Millen, White, Zelano, & Branigan

[57] ABSTRACT

The invention relates to a shock wave or ultrasound work process wherein shock wave or ultrasound generators are used to produce shock waves or ultrasound in a medium in which an effect is to be achieved, wherein to this medium is added a preparation which contains or produces microbubbles which cause an intensification of the shock wave or ultrasound effect, and to a preparation for carrying out the process wherein this preparation can also be used for the specific destruction of biological tissue with ultrasound and shock waves.

32 Claims, No Drawings

ULTRASOUND OR SHOCK WAVE WORK PROCESS AND PREPARATION FOR CARRYING OUT SAME

An important field of application of ultrasound technology is the examination of material without destroying same. In the Taschenbuch Akustik—Berlin: Verlag Technik 1984, H. O. Richter describes the ultrasound material examination; and, in this report, the coupling technique is explained, i.e., the coupling of the ultrasound vibrator to the test specimen.

In the journal "ULTRASONICS", July 1985, pp. 170-172, a process is described wherein a glass plate is cleaned in water by means of an ultrasound field. In the water, air bubbles are produced by ultrasound wherein the diameter of these bubbles is greater than that of the air bubbles which are produced by the basic frequency (25 kHz) of the irradiated ultrasound field. The first harmonic (47.2 kHz) of the irradiated ultrasound field acts as a surface wave on the boundary surface water/air of the air bubbles and produces secondary microbubbles whose diameter is smaller than that of the microbubbles which are produced only by the first harmonic. The coating material on the glass plate is removed by this small bubble system. With this process, high-energy ultrasound fields must be irradiated, which is not tolerated by all materials.

The object of the present invention is to improve the ultrasound work process by providing a special process and preparation for carrying out this process whereby good results can be achieved using less energy than with known processes and, in particular, through using shock waves.

According to the invention, this is achieved through the use of a preparation containing and/or producing microbubbles, added with or without microparticles to the medium, and the size of the microbubbles and the frequency range of the ultrasound field are attuned with each other so that the resonance frequency of the microbubbles lies in the frequency range of the ultrasound field.

The preparations containing or producing the microbubbles are applied to the medium in which the desired work is to be carried out or a predetermined action is to be achieved whereby the action of the irradiated shock waves or ultrasound fields is synergistically improved. The same effects are achieved with less irradiated energy. Greater effects are produced with the same energy.

For ultrasound irradiation, it is particularly advantageous to set the size of the microbubbles so that their resonance frequency lies in the frequency range of the ultrasound.

With the work process, the shock waves or ultrasound field is radiated by focusing generators into the medium into which the preparations containing or producing the microbubbles are introduced.

Shock waves or ultrasound fields are advantageously irradiated into a predetermined area by generators from different directions. It is further proposed to swivel the generator(s) of the shock waves or ultrasound fields around the focus.

Of special significance is the intensifying action with surface treatments of workpieces, such as surface tempering and the like, by means of shock waves or ultrasound. A further area of application is shock wave or ultrasound cleaning wherein the shock wave or ultrasound energy is radiated via the base and walls of a cleaning tank or via suspended generators into the cleaning fluid. The material to be cleaned can be brought into the cleaning fluid in cages or drums and, in the case of large installations, through a conveyor system. By using the preparation containing or producing the microbubbles according to the invention, it is possible to reduce cleaning times quite considerably and to achieve an extremely clean-pore surface.

The process according to the invention can also be used in the case of disintegration which comprises the use of shock waves or power ultrasound for extraction, dispersion (emulsification, homogenization), and for other processes. With this process, it is possible to break down microorganisms such as bacteria, viruses and fungi. Ingredients can be extracted from plant and animal materials. Substances which are difficult to dissolve can be emulsified in liquids, and solid, insoluble materials can be finely dispersed in liquids. Furthermore, chemical and biological reactions can be accelerated and samples can be prepared for microscopic and electron-microscopic investigations.

In the case of extraction, cavitation can lead to a breakdown of the cells or substance and to the dispersion of the suspended solid particles in conjunction with an increased mass transport through an acoustic current. Through the process according to the invention, increased extraction rates are achieved in extraction of sugar from sugar beets, hops extraction, protein precipitation in the beer brewing process, in the extraction of oil from oil seeds and fish and in the extraction of alkaloids from plant materials and in the extraction of ores.

Furthermore, in the case of dispersion, solid particles (and, similarly, liquids) can be dispersed into another carrier through shock wave or ultrasound energy. This makes it possible to produce the finest color distribution in solutions, simplifies the production of pharmaceutical products and also simplifies the splitting of cellulose fibers.

An advantageous field of use of the process according to the invention comprises emulsification to produce mixed products, for example, the raw materials of margarine. The process can also be used in the cosmetics industry.

The process according to the invention is also suitable for shock wave or ultrasound application in the textile and paper industries. More particularly, it is possible to carry out preliminary treatments on cellulose fibers or cellulose-containing substances with shock waves or ultrasound using the preparations containing or producing microbubbles. A further field of use is the defoaming carried out in industrial processes and in purification plants. More particularly, the treatment of waste water can be improved, which is particularly important for the protection of the environment.

Advantageously,
1. a suspension with microbubbles consisting of microparticles of a boundary surface active substance in a fluid carrier or
2. a suspension with microbubbles consisting of microparticles of a non-boundary surface active solid in a fluid carrier or
3. a suspension with microbubbles consisting of microparticles of a mixture of at least one boundary surface active substance with a non-boundary surface active solid in a fluid carrier can be used for the shock wave or ultrasound work process.

Some of these preparations used according to the invention are described in EP OS 122 624 and 123 235.

Advantageously, the preparation used can contain microparticles which contain a boundary surface active substance, lecithins, polyoxyethylene fatty acid esters, glycerin polyethylene glycol ricinoleate, polyoxymethylene-polyoxypropylene polymers, saccharose esters, xyloglycerides, saturated or unsaturated $C_{4-20}$-fatty alcohols, saturated or unsaturated $C_{4-20}$-fatty acids or their salts, mono-, di- and triglycerides, fatty acid esters as microparticles. Furthermore, the preparation can contain microparticles which contain as a boundary surface active substance soya oil, saccharose glyceride or polyethylene glycol sorbitan monostearate.

It can be particularly advantageous if magnesium stearate, ascorbyl palmitate, saccharose monopalmitate, saccharose monostearate, saccharose distearate or butyl stearate are contained in the preparation as boundary surface active substances.

The suspension with microbubbles contains the boundary surface active substance in a concentration of from 0.001 to 5 percent by weight, preferably from 0.04 to 1 percent by weight.

The preparation can advantageously contain as non-boundary surface active solids cyclodextrins, monosaccharides, disaccharides, trisaccharides, polyols or inorganic or organic salts with a concentration of from 2 to 50 percent by weight, preferably from 9 to 40 percent by weight. The preparation can further contain microparticles which contain as a non-boundary surface active solid dextrose, maltose, galactose, lactose or a cyclodextrin in a concentration of from 2 to 50 percent by weight, preferably 9 to 40 percent by weight.

Sodium chloride, sodium citrate, sodium acetate or sodium tartrate can be named as suitable inorganic or organic salts.

The preparation used can advantageously contain as a fluid carrier water; an electrolyte solution; an aqueous solution of single or multivalent alcohols or polyether alcohols or an aqueous solution of a mono-, disaccharide or Ringer solution or Tyrode solution; or an aqueous solution of maltose, dextrose, lactose or galactose. The fluid carrier can contain with particular advantage glycerine, polyethylene glycol or propylene glycol methylether.

However, a sodium chloride solution can also be contained in the preparation as the fluid carrier.

It surprisingly has also been found that a preparation used according to the invention which contains microparticles of maltose, dextrose, lactose or galactose in a fluid carrier, which can be water, a physiological electrolyte solution such as a 0.9% aqueous sodium chloride solution, Ringer solution or Tyrode solution, or an aqueous solution of maltose, dextrose, lactose or galactose, allows an intensification of the effect of the shock wave and ultrasound work process without the addition of viscosity-increasing substances, such as, for example, propylene glycol.

Preparations of this kind used according to the invention are described in EP OS 131 540.

The preparation used according to the invention can, therefore, contain microparticles of lactose in up to 25% (by weight) of an aqueous lactose solution. More particularly, the preparation used according to the invention can also contain microparticles of galactose in up to 20% aqueous galactose solution or microparticles of galactose in water.

Furthermore, it is proposed that the preparation contain microparticles of a mixture of butyl stearate and galactose in water or a mixture of soya oil, saccharose glyceride and galactose in water or polyethylene glycol sorbitan monostearate and galactose in a physiological sodium chloride solution or oleic acid and galactose in a physiological sodium chloride solution.

It is further within the scope of the invention that a preparation used according to the invention be a fluid solution with microbubbles consisting of a mixture of 0.01 to 10 percent by weight of a tenside or tenside mixture with an aqueous carrier fluid or one which is miscible with water, and a mixture of 0.5 to 50 percent by weight of a viscosity-increasing substance or substance mixture in an aqueous or water-miscible carrier solution wherein the mixtures are separate or combined.

A preparation which can be used with particular advantage for the shock wave and ultrasound work process comprises a mixture of 0.01 to 10 percent by weight of a tenside or tenside mixture in an aqueous or water-miscible carrier fluid which contains 0.05 to 5 percent by weight of a physiologically compatible carbonate and the mixture of 0.5 to 50 percent by weight of a viscosity-increasing substance or a substance mixture with an aqueous or water-miscible carrier fluid which contains an amount of physiologically compatible acid equivalent to the carbonate.

Sodium hydrocarbonate and potassium hydrocarbonate are particularly useful as the carbonate. Lactic acid, citric acid and pyroracemic acid are mentioned in particular as the acids.

Preparations of this kind used according to the invention are described in EP PS 0 077 752.

Both ionogenic and non-ionogenic tensides, which can also act at the same time to increase viscosity, are suitable as the tensides. Non-ionogenic tensides can be: lecithins, lecithin fractions and their modification products; polyoxyethylene fatty acid esters, such as polyoxyethylene fatty alcohol ether, polyoxyethylated sorbitan fatty acid ester, glycerine-polyethylene glycoloxystearate, glycerine polyethylene glycol ricinoleate, ethoxylated soya sterines, and ethoxylated castor oils and their hydrated derivatives; cholesterol; polyoxyethylene-polyoxypropylene polymers fatty acid stearates and polyoxyethylene-polyoxypropylene polymers with a molecular weight of 6800–8975, 13300 and 16250, are preferred.

Ionogenic tensides can be quaternary ammonium base, sodium lauryl sulfate, and sodium dioctylsulfosuccinate.

Viscosity-increasing substances can be mono- or polysaccharides such as glucose, levulose, galactose, lactose, sorbite, mannite, xylite, saccharose or dextran; cyclodextrins; hydroxyethyl starch; and polyols. Glycerin, polyglycols, inulin and 1,2-propane diol are used as polyols. To increase the viscosity, it is also possible to use proteins, protein-like substances, amino acids or blood substitutes such as, for example, plasma proteins, gelatins, oxypolygelatins and gelatin derivatives or their mixtures.

The concentration of these substances in the solution can amount to 0.5 to 50 percent by weight, wherein the maximum concentration also depends on the substance dissolved. Thus, for example, glucose or lactose can be used with a concentration of from 0.5 to 50 percent by weight, while gelatin has a preferred concentration of 0.5 to 2 percent by weight. The oxypolygelatin is preferably used with a concentration of from 0.5 to 10 percent by weight.

It is also possible to use tensides which have at the same time a viscosity-increasing effect, such as, for example, polyoxyethylene-polyoxypropylene polymers with a molecular weight of 4750 to 16250.

In this case, the concentration of the tensides with the viscosity-increasing effect amounts to 1 to 20 percent by weight, preferably 3 to 10 percent by weight. The tenside or tenside mixture is preferably dissolved in a carrier fluid in the presence of the viscosity-increasing substance or substance mixtures.

As the carrier fluid, it is possible to use water or aqueous solutions, water-miscible single or multivalent alcohols, Ringer solution, Tyrode solution or the aqueous solutions of sodium chloride, calcium chloride, sodium hydrocarbonate, sodium citrate, sodium acetate or sodium tartrate or salt solutions, such as those usually used as infusion solutions, or mixtures thereof.

It has surprisingly been shown that it is particularly advantageous, in order to break down biological tissue using the process according to the invention, to apply at least one of the preparations previously listed to the area of the tissue which is to be destroyed.

It is particularly advantageous to apply to the area of the tissue which is to be destroyed microbubbles having a resistant, coalescent surface membrane and containing a number of non-toxic and non-antigenic organic molecules which contain a gas of a selected composition. The diameter of the microbubbles is no greater than 300 microns and no smaller than 0.5 microns. More particularly, the molecules of the surface membrane have a hydrophilic and a hydrophobic section wherein the hydrophilic section is aligned radially from the center of a microbubble. With particular advantage, a surface membrane is used for the microbubbles which consists of a gellable composition, more particularly gelatin. Microbubbles of this kind used according to the invention are described in U.S. Pat. No. 4,276,885.

EP 0 284 802 describes the destruction of biological cells, more particularly tumors wherein the cells are marked with metal particles and exposed to shock waves and/or ultrasound. These microparticles are impinged by the ultrasound or shock wave energy so that they help like shot or shrapnel to break down the tissue.

According to a further embodiment, preparations are produced which exert a synergistic effect for the therapy of tumor tissue and/or tumor cells or other type of pathological tissue cells with shock waves or ultrasound waves.

It was surprisingly found that all the preparations listed above produce excellent results in the case of shock waves and ultrasound therapy of pathological tissue, particularly tumors.

If microbubbles which have a coalescent-resistant surface membrane containing a number of non-toxic and non-antigenic organic molecules are used, then it is advantageously possible for the intended use of these microbubbles to set the diameter in the range of from 300 to 0.05 micron. It is thereby possible to apply these microbubbles to the specific areas of the body. By fixing the diameter of the bubbles, it is possible to determine which parts of the tissue the bubbles can penetrate and which parts they cannot. The use of microbubbles whose surface membrane consists of a gellable composition, such as gelatin, is particularly advantageous.

EXAMPLES

Example 1

Leukemia cells embedded in gelatin are placed in a specimen bottle in a water bath provided with a spark discharge shock wave generator. The specimen bottle is then brought into the second focal point of the ellipsoid and exposed to the shock waves (250 pulses).

Example 2

In an analogous way, a similar number (as mentioned in Example 1) of leukemia cells embedded in gelatin and a suspension of galactose microparticles and microbubbles in a 20% aqueous galactose solution are placed in the specimen bottle and likewise exposed to 250 pulses of shock waves.

The intact cells of Examples 1 and 2 still existing after the shock wave treatment are then counted by means of a cell counting device (fluorescence process). It was thereby determined by 0% of the original cells of Example 1 and 15% of the cells of Example 2 had been destroyed.

I claim:

1. In a method for destroying tumor tissue, cells or other pathological tissue cells by means of shock waves or ultrasound, comprising subjecting said tissue or cells to shock waves or ultrasound field, wherein the improvement comprises that said tissue or cells are subjected to said shock waves or ultrasound in a preparation containing or producing microbubbles.

2. A method according to claim 1, wherein the shock waves or ultrasound field are focused on an area.

3. A method according to claim 2, wherein the shock waves or ultrasound field are radiated into the area by generators from different directions.

4. A method according to claim 1, wherein a generator of the shock waves or ultrasound field is swivelled about a focal point of said shock waves and ultrasound field.

5. A method according to claim 1, wherein the preparation is a suspension with microbubbles consisting essentially of microparticles of a boundary surface active substance in a fluid carrier.

6. A method according to claim 5, wherein the boundary surface active substance is a lecithin, polyoxyethylene fatty acid ester, glycerins polyethylene glycol ricinoleate, polyoxyethylene polyoxypropylene polymer, saccharose ester, xyloglyceride, saturated or unsaturated $C_{4-20}$-fatty alcohol, saturated or unsaturated $C_{4-20}$-fatty acid or a salt thereof, a mono- or di- or triglyceride, fatty acid ester, soya oil saccharose, glyceride or polyethylene glycol sorbitan monostearate as microparticles in a concentration of 0.001 to 10 percent by weight.

7. A method according to claim 5, wherein the boundary surface active substance is magnesium stearate, ascorbyl palmitate, saccharose monopalmitate, saccharose monostearate, saccharose distearate or butyl stearate in a concentration of 0.001 to 10 percent by weight.

8. A method according to claim 5, wherein the fluid carrier is physiologically compatible and is water, physiological electrolyte solution, an aqueous solution of single or multivalent alcohols or polyether alcohols or the aqueous solution of a mono- or disaccharide.

9. A method according to claim 5, wherein the fluid carrier is Ringer solution or Tyrode solution or an aqueous solution of maltose, dextrose, lactose or galactose.

10. A method according to claim 5, wherein the fluid carrier is an aqueous solution of glycerine, polyethylene glycol or propylene glycol methyl ether.

11. A method according to claim 5, wherein the preparation contains microparticles of a mixture of polyethylene glycol sorbitan monostearate and galactose in physiological sodium chloride solution.

12. A method according to claim 1, wherein the preparation is a suspension with microbubbles of a non-boundary surface active solid in a fluid carrier.

13. A method according to claim 12, wherein the non-boundary surface active solid is a cyclodextrin, monosaccharide, trisaccharide, polyol, or organic or inorganic salt thereof, with a concentration of 2 to 50 percent by weight.

14. A method according to claim 12, wherein the preparation contains microparticles of galactose in water.

15. A method according to claim 12, wherein the preparation contains microparticles of galactose in up to 20% by weight aqueous solution.

16. A method according to claim 12, wherein the preparation contains microparticles of lactose in up to 25% (by weight) aqueous solution.

17. A method according to claim 1, wherein the preparation is a suspension with microbubbles consisting essentially of microparticles of a mixture of at least one boundary surface active substance with a non-boundary surface active solid in a fluid carrier.

18. A method according to claim 12, wherein the non-boundary surface active solid is galactose, dextrose, maltose, lactose or a cyclodextrin in a concentration of 2 to 50 percent by weight.

19. A method according to claim 17, wherein the preparation contains microparticles of a mixture of butyl stearate and galactose in water.

20. A method according to claim 17, wherein the preparation contains microparticles of a mixture of oleic acid and galactose in physiological sodium chloride solution.

21. A method according to claim 1, wherein the preparation is a fluid solution with microbubbles consisting essentially of (a) a mixture of 0.1 to 10 percent by weight of a tenside or tenside mixture with an aqueous or water-miscible carrier fluid; and (b) a mixture of 0.5 to 50 percent by weight of a viscosity-enhancing substance or a substance mixture in an aqueous or water-miscible carrier fluid or a combination of (a) and (b).

22. A method according to claim 21, wherein the mixtures consist essentially of
(a) 0.1 to 10 percent by weight of a tenside or tenside mixture in an aqueous or water-miscible carrier fluid which contains 0.05 to 5 percent by weight of a physiologically compatible carbonate; and
(b) a mixture of 0.5 to 50 percent by weight of a viscosity-increasing substance or a substance mixture with an aqueous or water-miscible carrier fluid which contains the amount of physiologically compatible acid which is equivalent to the carbonate.

23. A method according to claim 21, wherein the preparation contains a non-ionogenic tenside which is a polyoxyethylene polyoxypropylene polymer which has a simultaneous viscosity-increasing effect.

24. A method according to claim 23, wherein the tenside consists essentially of polyoxyethylene polyoxypropylene polymers with the molecular weight 6800 to 8975 or which consists essentially of a polyoxyethylene fatty acid ester.

25. A method according to claim 21, wherein the preparation contains a tenside which consists essentially of polyoxyethylene stearates, sodium lauryl sulfate or sodium dioctyl sulfosuccinate.

26. A method according to claim 21, wherein the carrier fluid is water or a water-miscible single or multivalent alcohol, physiological electrolyte solution an infusion solution or a mixture thereof.

27. A method according to claim 1, wherein the microbubbles have a coalescent resistant surface membrane in which there are a number of non-toxic and non-antigenic organic molecules and which contains a gas of a selected composition and wherein the diameter of the microbubbles is no greater than 300 micron and no smaller than 0,5 micron.

28. A method according to claim 27, wherein the molecules of the surface membrane have a hydrophilic and a hydrophobic section and their hydrophilic section is directed radially away from the center of a microbubble.

29. A method according to claim 27, wherein the surface membrane for the microbubbles consist essentially of a gellable composition.

30. A method according to claim 29, wherein the gellable composition is gelatin.

31. A method according to claim 1, wherein the preparation contains microparticles.

32. A method according to claim 1, wherein the size of the microbubbles and the frequency range of the ultrasound field are attuned with each other so that the resonance frequency of the microbubbles lies in the frequency range of the ultrasound field.

* * * * *